(12) United States Patent
Eder et al.

(10) Patent No.: US 7,809,445 B2
(45) Date of Patent: Oct. 5, 2010

(54) MEASUREMENT OF EVOKED NEURAL RESPONSE

(75) Inventors: Helmut Christian Eder, Castle Hill (AU); Padraig Joseph Hurley, Redfern (AU); David Kerry Money, Pennant Hills (AU); Tony Mikeal Nygard, Kariong (AU)

(73) Assignee: Cochlear Limited, Lane Cove, NSW (AU)

( * ) Notice: Subject to any disclaimer, the term of this patent is extended or adjusted under 35 U.S.C. 154(b) by 0 days.

(21) Appl. No.: 10/526,492

(22) PCT Filed: Sep. 4, 2003

(86) PCT No.: PCT/AU03/01151

§ 371 (c)(1),
(2), (4) Date: Aug. 23, 2005

(87) PCT Pub. No.: WO2004/021885

PCT Pub. Date: Mar. 18, 2004

(65) Prior Publication Data

US 2006/0089561 A1    Apr. 27, 2006

(30) Foreign Application Priority Data

Sep. 4, 2002   (AU) .............................. 2002951218

(51) Int. Cl.
*A61N 1/00* (2006.01)
(52) U.S. Cl. ............................. 607/57; 607/55; 381/312
(58) Field of Classification Search ................ 381/317, 381/312; 455/130, 227; 375/316; 600/544, 600/545, 554, 559; 607/55–57
See application file for complete search history.

(56) References Cited

U.S. PATENT DOCUMENTS

| 452,003 | A | 5/1891 | Lipe |
| 3,043,000 | A | 7/1962 | Hatfield |
| D227,118 | S | 6/1973 | Muraoka |
| 3,771,685 | A | 11/1973 | Micallef |

(Continued)

FOREIGN PATENT DOCUMENTS

EP    0282336    9/1988

(Continued)

OTHER PUBLICATIONS

Brown, et al., The Relationship Between EAP and EABR Thresholds and Levels Used to Program the Nucleus 24 Speech Processor: Data from Adults, Ear and Hearing, vol. 21 (2), Apr. 2000, pp. 151-163.

(Continued)

*Primary Examiner*—Nay A Maung
*Assistant Examiner*—Richard Chan
(74) *Attorney, Agent, or Firm*—Connolly Bove Lodge & Hutz LLP

(57) ABSTRACT

A method and device for measuring an evoked neural response comprising a sensor (25) for obtaining a sensed signal representing the evoked neural response, a high gain amplifier (30) having a signal input (31) for receiving the sensed signal and having a reference input (32), and means for altering or setting a reference voltage at the reference input (32) to prevent the amplifier (30) saturating with variations of the sensed signal.

18 Claims, 4 Drawing Sheets

U.S. PATENT DOCUMENTS

| | | | |
|---|---|---|---|
| 4,003,521 A | | 1/1977 | Hess |
| 4,114,627 A | | 9/1978 | Lewyn et al. |
| 4,226,164 A | | 10/1980 | Carter |
| 4,240,428 A | | 12/1980 | Akhavi |
| 4,305,396 A | | 12/1981 | Wittkampf et al. |
| 4,343,312 A | | 8/1982 | Cals et al. |
| D267,541 S | | 1/1983 | Kanemitsu et al. |
| 4,373,531 A | | 2/1983 | Wittkampf et al. |
| 4,414,701 A | | 11/1983 | Johnson |
| 4,532,930 A | | 8/1985 | Crosby et al. |
| 4,543,956 A | | 10/1985 | Herscovici |
| 4,610,621 A | | 9/1986 | Taber et al. |
| 4,731,718 A | | 3/1988 | Sheu et al. |
| 4,895,152 A | | 1/1990 | Callaghan et al. |
| 4,917,504 A | | 4/1990 | Scott et al. |
| 4,920,679 A | | 5/1990 | Sarles et al. |
| 5,014,592 A | | 5/1991 | Zweig et al. |
| 5,016,280 A | * | 5/1991 | Engebretson et al. ....... 381/320 |
| 5,034,918 A | | 7/1991 | Jeong et al. |
| 5,172,690 A | | 12/1992 | Nappholz et al. |
| 5,278,994 A | | 1/1994 | Black et al. |
| D348,067 S | | 6/1994 | Lucey et al. |
| 5,565,503 A | | 10/1996 | Garcia et al. |
| 5,674,264 A | | 10/1997 | Carter et al. |
| 5,758,651 A | * | 6/1998 | Nygard et al. ............... 600/554 |
| 5,775,652 A | | 7/1998 | Crawshaw et al. |
| 5,785,477 A | | 7/1998 | McGuffey et al. |
| 5,895,416 A | | 4/1999 | Barreras, Sr. et al. |
| 5,963,904 A | | 10/1999 | Lee et al. |
| 5,971,334 A | | 10/1999 | Crawshaw et al. |
| 5,999,856 A | * | 12/1999 | Kennedy ..................... 607/57 |
| 6,035,001 A | * | 3/2000 | Eklund et al. ............... 375/316 |
| 6,044,162 A | * | 3/2000 | Mead et al. ................. 381/312 |
| 6,073,973 A | | 6/2000 | Boscaljon et al. |
| 6,151,400 A | * | 11/2000 | Seligman ................... 381/317 |
| 6,157,861 A | | 12/2000 | Faltys et al. |
| 6,205,360 B1 | | 3/2001 | Carter et al. |
| 6,428,484 B1 | | 8/2002 | Battmer et al. |
| 6,430,402 B1 | | 8/2002 | Agahi-Kesheh |
| 6,463,328 B1 | | 10/2002 | John |
| 6,537,200 B2 | | 3/2003 | Leysieffer et al. |
| 6,571,676 B1 | | 6/2003 | Folsom et al. |
| 6,575,894 B2 | | 6/2003 | Leysieffer et al. |
| 6,600,955 B1 | | 7/2003 | Zierhofer |
| 6,697,674 B2 | | 2/2004 | Leysieffer |
| 6,751,505 B1 | | 6/2004 | Van Den Honert et al. |
| 6,892,092 B2 | | 5/2005 | Palreddy et al. |
| 2001/0049466 A1 | | 12/2001 | Leysieffer et al. |
| 2004/0098063 A1 | | 5/2004 | Goetz |
| 2005/0101878 A1 | | 5/2005 | Daly et al. |
| 2005/0245991 A1 | | 11/2005 | Faltys et al. |

FOREIGN PATENT DOCUMENTS

| | | |
|---|---|---|
| GB | 0414579 | 8/1934 |
| GB | 2266045 | 10/1993 |
| WO | 9210134 | 6/1992 |
| WO | WO 92/10134 | 6/1992 |
| WO | 9324176 | 12/1993 |
| WO | 9414376 | 7/1994 |
| WO | WO 94/14376 | 7/1994 |
| WO | 9501709 | 1/1995 |
| WO | 9612383 | 4/1996 |
| WO | 9709863 | 3/1997 |
| WO | 9748447 | 12/1997 |
| WO | 0076436 | 12/2000 |
| WO | 0113991 | 3/2001 |
| WO | 02082982 | 10/2002 |
| WO | 03070322 | 8/2003 |
| WO | 2004021885 | 3/2004 |

OTHER PUBLICATIONS

Charasse, et al., "Automatic analysis of auditory nerve electrically evoked compound action potential with an artificial neural network," Artificial Intelligence in Medicine, 2004 31, 221-229.

Delgado, et al., "Automated Auditory Brainstem Response Interpretation," IEEE Engineering in Medicine and Biology, Apr./May 1994.

Charasse, et al., "Comparison of Two Different Methods to Automatically Classify Auditory Nerve Responses Recorded with NRT System," Acta Acustica United with Acustica, vol. 99 (2004) 512-519.

Seyle, et al., "Speech Perception Using Maps Based on Neural Response Telemetry Measures," Ear & Hearing, Copyright © 2002 by Lippincott Williams & Wilkins.

Vannier, et al., "Objective detection of brainstem auditory evoked potentials with a priori information from higher presentation levels," Artificial Intelligence in Medicine 25, (2002) 283-301.

Franck, et al., "Estimation of Psychophysical Levels Using the Electrically Evoked Compound Action Potential Measured with the Neural Response Telemetry Capabilities of Cochlear Corporation's C124M Device," Ear & Hearing, Copyright © 2001 by Lippincott Williams & Wilkins.

Dijk et al., "Development of a Prototype Fully-Automated Intra-Operative ECAP Recording Tool, Using NRT(TM) v3," 2003 Conference on Implantable Auditory Prostheses (Asilomar), 2003, 7 pages total.

Hughes, et al, Comparison of EAP Thresholds with MAP Levels in the Nucleus 24 Cochlear Implant: Data from Children [Articles], Ear and Hearing, vol. 21 (2), Apr. 2000, pp. 164-174.

Abbas et al., "Electrically Evoked Compound Action Potentials Recorded from Subjects Who Use the Nucleus CI24M Device," 2000, Gantz et al. Seventh Symposium on Cochlear Implants in Children, pp. 6-9.

Baumgarte, et al., "A Nonlinear Psychoacoustic Model Applied to the ISO MPEG Layer 3 Coder," Proc. 99th Conv. Aud. Eng. Soc., New York, NY, Oct. 1995, preprint 4087.

Edler, et al., "ASAC-Analysis/Synthesis Audio Codec for Very Low Bit Rates," Proc. 100th Conv. Aud. Eng. Soc., May 1996, preprint 4179.

Cohen, et al., "Spatial spread of neural excitation in cochlear implant recipients: comparison of improved ECAP method and psychophysical forward masking," Hearing Research, 179 (2003) 72-87.

Cohen, et al., "Spatial spread of neural excitation: comparison of compound action potential and forward-masking data in cochlear implant recipients," International Journal of Audiology 2004: 43: 346-355.

Miller, et al., "An Improved Method of Reducing Stimulus Artifact in the Electrically Evoked Whole-Nerve Potential," Ear & Hearing, Copyright © 2000 by Lippincott Williams & Wilkins, USA.

European Search Report, EP 01 95 9971, dated Aug. 11, 2005.

International Preliminary Examination Report, PCT/AU01/01032, dated Apr. 10, 2002.

International Search Report, PCT/AU01/01032, dated Oct. 5, 2001.

International Search Report and Written Opinion, PCT/US05/21207 dated Feb. 8, 2006.

International Preliminary Examination Report, PCT/AU02/00500, dated Feb. 12, 2003.

International Search Report, PCT/AU02/00500, dated Jun. 26, 2002.

Supplementary Partial European Search Report, EP 02 71 7863 dated Oct. 18, 2005.

Hartmann, et al., "Evoked Potentials from the Auditory Nerve Following Sinusoidal Electrical Stimulation of the Cochlea: New Possibilities for Preoperative Testing in Cochlear-Implant Candidates?" Acta Otoloaryngol (Stockh) 1994; 114, Scandinavian University Press ISSN 0001-648, pp. 495-500.

\* cited by examiner

MEASUREMENT OF EVOKED NEURAL RESPONSE

CROSS-REFERENCE TO RELATED APPLICATIONS

This application claims the priority of and is a national stage application of PCT Application No. PCT/AU2003/00001151, entitled, "Method and Apparatus for Measurement Of Evoked Neural Response," filed on Sep. 4, 2003, which claims the priority of Australian Patent No. 2002951218, filed on Sep. 4, 2002. The entire disclosure and contents of the above applications are hereby incorporated by reference.

FIELD OF THE INVENTION

The present invention relates to measurement of a neural response evoked by a stimulus, and in particular to a method and device for measuring the evoked neural response in the presence of stimulus artefacts.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which comprise a microphone and an amplifier for amplifying detected sounds so that acoustic information does reach the cochlea and the hair cells.

In many people who are profoundly deaf, the reason for deafness is sensorineural hearing loss, which is caused by an absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner. It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two essential components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of an RF link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

As the implant is surgically implanted within the recipient, there is a need to obtain data about the actual performance of the electrode array following implantation go as well as the response of the auditory nerve to stimulation. Such data collection enables detection and confirmation of the normal operation of the device, and allows the stimulation parameters to be optimised to suit the needs of the patient.

Typically, following the surgical implantation of the cochlear implant, the recipient must have the implant fitted or customised to conform with the specific recipient demands. This procedure collects and determines patient specific parameters such as threshold levels (T levels) and maximum comfort levels (C levels) for each stimulation channel. Essentially, this is manually performed by applying stimulation pulses for each channel and receiving an indication from the implant recipient as to the level and comfort of the resulting sound. For implants with a large number of channels for stimulation, this process is quite time consuming and rather subjective as it relies heavily on the recipient's subjective impression of the stimulation rather than any specific measurement. This aspect is further complicated in the case of children and prelingually or congenitally deaf patients who are unable to supply an accurate impression of the resultant hearing sensation, and hence fitting of the implant may be sub-optimal. In such cases an incorrectly fitted implant may result in the recipient not receiving optimum benefit from the implant and in the cases of children may directly hamper the speech and hearing development of the child.

Therefore, as previously mentioned, there is a need to obtain objective measurements of patient specific data especially in cases where an accurate subjective measurement is not possible.

One proposed method of interrogating the performance of the implanted device and making objective measurements of patient specific data such as T and C levels is to directly measure the response of the auditory nerve to an electrical stimulus. The measurement of Electrically Evoked Compound Action Potentials (ECAPs) provides an objective measurement of the response of the nerves to electrical stimulus. Following electrical stimulation, the neural response is caused by the superposition of single neural responses at the outside of the axon membranes. The ECAP can then be measured in response to various stimulations and from this the performance of the implant can be assessed and patient parameters can be interpolated.

Indeed, there is a need to measure the response of nerves to electrical stimulation in many applications, and not just in the area of cochlear implants. The measurement of ECAPs has proven to provide a useful objective measurement in many such applications. By measuring the ECAP in response to a stimulation, the effectiveness of the stimulation can be assessed in relation to the neural response evoked by the stimulation.

A number of ECAP measurement methods and devices have been developed which attempt to measure the response of the nerves to electrical stimulus. In the area of cochlear implants where electrical stimulus is delivered to the nerve cells within the cochlea, such systems have essentially attempted to use the electrodes implanted within the cochlea to both deliver stimulation and to detect the responses of the nerves to such stimulation.

U.S. Pat. No. 5,758,651 describes one system and apparatus for recovering ECAP data from a cochlear implant. This system measures the neural response to the electrical stimulation by using the stimulus array to not only apply the stimulation but to also detect and receive the response. In this system the array used to stimulate and collect information is a standard intra-cochlear and/or extra-cochlear electrode array. Following the delivery of a stimulation pulse via chosen stimulus electrodes, all electrodes of the array are open circuited for a period of time prior to and during measurement of the induced neural response. The purpose of open circuiting all electrodes during this period is to reduce the detected stimulus artefact measured with the ECAP nerve response.

Whilst prior art systems of this type have proven useful in capturing and investigating evoked neural responses in the cochlea, there are still a number of intrinsic limitations associated with such systems, which have affected the quality of the measurements of the neural response. In the main this has been due to the presence of stimulus artefacts in the measurement detected, resulting in a measurement being taken which is not necessarily a true indication of the actual ECAP response present.

The process of distinguishing the actual ECAP from stimulus artefacts has presented considerable difficulties, including problems such as the fact that the signals that are to be measured are extremely low level signals (down to the order of 10 uV). In cochlear implant applications in particular, an intra-cochlear electrode usually delivers a stimulus pulse with an amplitude typically in the range of 1V to 10V, which is many orders of magnitude greater than the ECAP response that is to be measured resulting from this stimulation.

Providing for a system that is firstly able to deliver a stimulus of sufficient amplitude and also to detect the elicited response of the nerves to that particular stimulation has therefore been problematic. Due to the nature of the neural response, the sensing system must be ready to record this response within a short delay (preferably less than 50 us) after completion of the stimulus. In order to properly resolve the very small neural signal a large amplifier gain is required (typically of about 60 dB to 70 dB), however the neural signal is often superimposed on a much larger artefact which makes it difficult to extract the neural signal of interest due to the finite dynamic range of the amplifier and the need for high gain to resolve the signal.

In the past, the only way useful measurements have been able to be obtained from the associated artefacts has been through the use of extensive post processing techniques. These techniques have attempted to apply complicated mathematical algorithms to the associated measurements in an attempt to cancel out the presence of the artefacts in the measurements. Such a system does not provide immediate results which can be acted upon, as the measured results often require time consuming analysis before they can be used. With the need to use such results immediately to adjust patient T and C levels, existing methods are not satisfactory.

Similar needs exist in respect of measurement of neural responses evoked by other types of devices.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of each claim of this application.

SUMMARY OF THE INVENTION

According to a first aspect, the present invention provides a method of measurement of an evoked neural response comprising the steps of:

obtaining a sensed signal representing the evoked neural response from a sensor;

passing the obtained sensed signal to a signal input of a high gain amplifier; and altering a reference voltage of the high gain amplifier in order to prevent the high gain amplifier saturating with variations of the sensed signal.

A reference to altering or adjusting the reference voltage of the high gain amplifier is equivalent to resetting the amplifier at specific intervals.

By resetting or altering the reference voltage of the amplifier during measurement, the present invention enables a high gain amplifier to be used in obtaining measurements of an evoked neural response, thus enabling detection of smaller neural response signals than prior art measurement methods. While resetting the reference voltage of the amplifier during measurement causes the output of the amplifier to represent the amplified sensed signal in piecewise fashion, the piecewise output signal segments can nevertheless be relatively easily reconstructed into a continuous waveform.

The step of altering the reference voltage of the high gain amplifier is preferably performed by setting the reference voltage to be equal to a present value of the sensed signal. This can be simply achieved by a sample-and-hold circuit having an input from the sensed signal. In such embodiments, a present dc-offset of the sensed signal is essentially removed, such that the high gain amplifier will only amplify and output variations of the sensed signal from the reference voltage. This enables such variations to be amplified by a relatively large amount, without the present dc-offset of the sensed signal and the slow variation of the signal causing the amplifier to enter saturation. It is to be appreciated that the present dc-offset is only "dc" when considered relative to the regularity with which the reference voltage of the high gain amplifier is altered.

Preferably, at the commencement of every sample period, the reference voltage of the high gain amplifier is altered to be equal to the present value of the sensed signal. In such embodiments of the invention, every sample obtained at the output of the high gain amplifier represents a change in the sensed signal which has occurred since the previous sample. With a sufficiently high sample rate, the change in the sensed signal during the duration of the sample period will be relatively small, enabling a larger gain to be applied to the signal without saturating the amplifier. Thus, even where a relatively large stimulus artefact contributes to the sensed signal and would otherwise cause saturation of the amplifier, the present invention enables high gain amplification of the sensed signal while avoiding saturation of the amplifier caused by large stimulus artefacts. That is, the method of the present invention assists in common mode rejection. In such embodiments of the present invention the obtained samples can simply be integrated or summed to obtain a continuous waveform representing the amplified sensed signal.

The step of obtaining may comprise obtaining a sensed signal of the neural response of an auditory nerve, obtained by one or more electrodes of an electrode array of a cochlear implant.

In accordance with a second aspect, the present invention provides a device for measuring an evoked neural response, the device comprising:

a sensor for obtaining a sensed signal representing the evoked neural response;

a high gain amplifier having a signal input for receiving the sensed signal, and having a reference input; and means for altering a reference voltage at the reference input of the high gain amplifier in order to prevent the high gain amplifier saturating with variations of the sensed signal.

The device may comprise a cochlear implant. In such embodiments the sensor may comprise one or more electrodes of an electrode array of an implanted portion of the cochlear implant. The cochlear implant may be a totally implanted cochlear implant, as described in PCT/AU01/00769 by the present applicant, the contents of which are incorporated herein by reference. While the present invention is advantageous when used in typical cochlear implants having a relatively simple implanted portion and an external processor, embodiments of the present invention in which the device is a totally implanted cochlear implant may be of particular advantage, in that processing of the sensed signal is performed prior to transmission of the obtained samples over a transcutaneous RF link, thus reducing the impact of noise of the RF link on the accuracy of the sampled data.

The present invention may be particularly advantageous when used in conjunction with stimulus artefact cancellation schemes. For example, the present invention, when combined with the artefact cancellation technique disclosed in International Application No. PCT/AU02/00500 by the present applicant, the contents of which are incorporated herein by reference, may enable particularly accurate high resolution measurements of an evoked neural response to be obtained, despite the relatively small amplitude of the neural response and the presence of stimulus artefacts of significantly larger amplitude. For example, embodiments of the present invention may obtain samples of the amplified sensed signal from the output of the high gain amplifier, and as each sample is obtained, transmit that sample across a transcutaneous RF link such that processing of the samples can be performed externally. Alternatively, where the implanted portion has processing capability, internal processing may be performed and may avoid the effects of noise of the RF link on each sample.

In accordance with a third aspect, the present invention provides a method of measurement of an evoked neural response comprising the steps of:

obtaining a sensed signal representing the evoked neural response from a sensor;

passing the obtained sensed signal to a signal input of a high gain amplifier; and setting a reference voltage of the high gain amplifier equal to a present value of the sensed signal in order to prevent the high gain amplifier saturating with variations of the sensed signal.

In accordance with a fourth aspect, the present invention provides a device for measuring an evoked neural response, the device comprising:

a sensor for obtaining a sensed signal representing the evoked neural response;

a high gain amplifier having a signal input for receiving the sensed signal, and having a reference input; and means for setting a reference voltage at the reference input of the high gain amplifier equal to a present value of the sensed signal in order to prevent the high gain amplifier saturating with variations of the sensed signal.

BRIEF DESCRIPTION OF THE DRAWINGS

Examples of the invention will now be described with reference to the accompanying drawings in which.

DETAILED DESCRIPTION OF THE PREFERRED EMBODIMENTS

Figure 1:
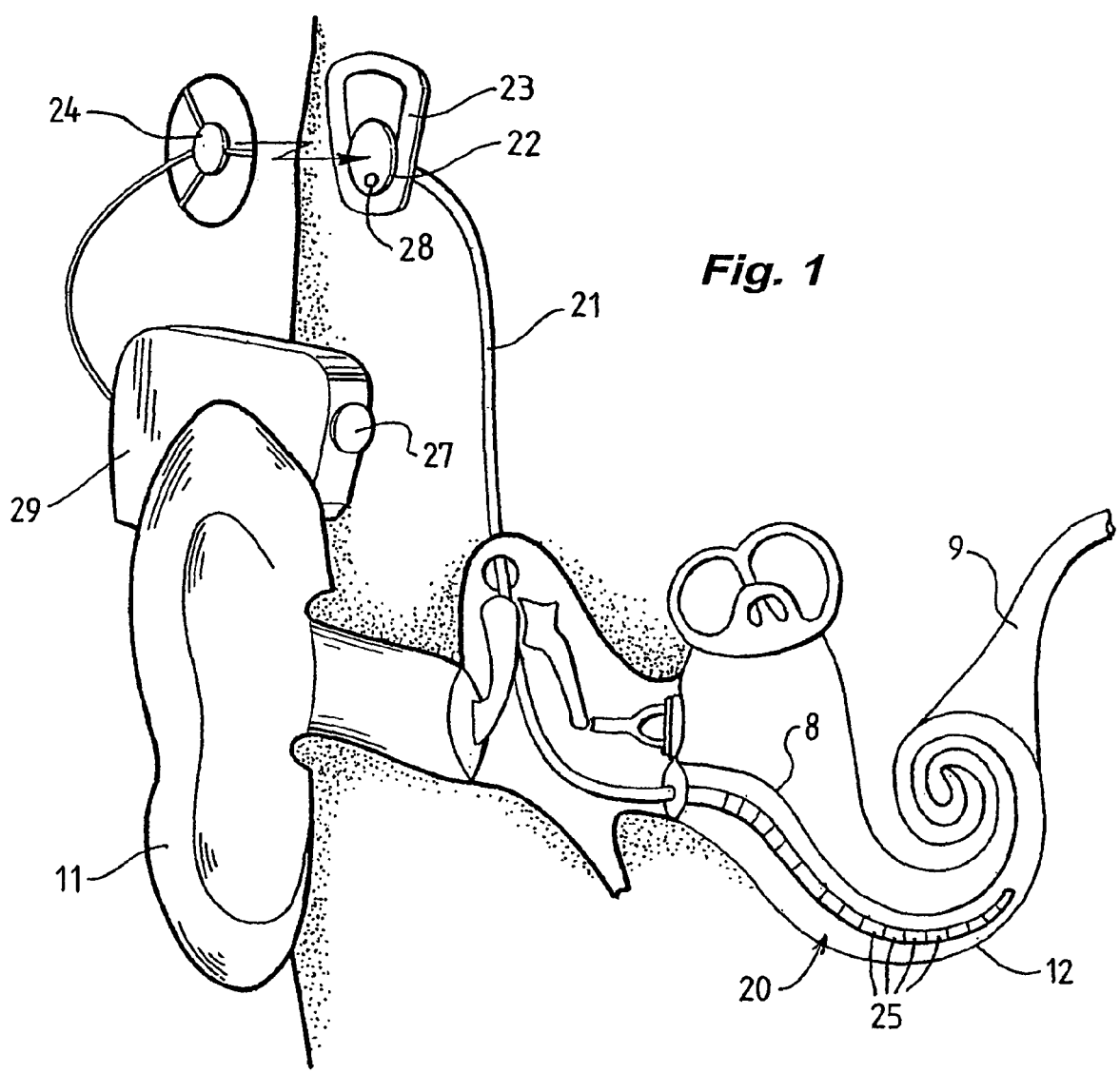
FIG. 1 is a pictorial representation of a cochlear implant system within which the present invention may be implemented.

While the present invention is not directed solely to a cochlear implant, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn elsewhere on the recipient's body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20, comprising, for example, twenty two intra-cochlear electrodes 25. One or more extra-cochlear electrodes 28 are also provided. The signals received via the RF link are applied by the array 20 to the basilar membrane 8 and the nerve cells within the cochlea 12 thereby stimulating the auditory nerve 9. The operation of such a device is described, for example, in U.S. Pat. No. 4,532,930. As depicted diagrammatically in FIG. 1, the cochlear implant electrode array 20 has traditionally been inserted into the initial portion of the scala tympani of the cochlea 12 up to about a full turn within the cochlea.

A sound processor (not shown) of the external component 29 includes an amplifier and a speech processor that uses a coding strategy to extract speech from the sounds detected by the microphone 27. In the depicted embodiment, the speech processor of the cochlear implant can perform an audio spectral analysis of the acoustic signals and output channel amplitude levels. The sound processor can also sort the outputs in order of magnitude, or flag the spectral maxima as used in the SPEAK strategy developed by Cochlear Ltd. Other coding strategies could be employed.

Whilst the system shown in FIG. 1 employs both implanted components and external components to perform its function, it should be appreciated that a totally implanted system could also be used to perform the same function. Such a system has been described in the applicant's co-pending International Patent Application No. PCT/AU01/00769, which is incorporated herein by reference, and describes a system wherein each of the components are provided implanted within the recipient to provide a device that can function in a mode that is substantially "invisible" to a casual onlooker.

An important feature of some implantable medical devices, such as those developed by the present applicant, is the ability of the device to not only deliver electrical stimulation via an electrode array 20 as depicted in FIG. 1, but to also use the array to measure responses of the surrounding nerves to the applied stimulation. Such a feature has been developed by the present applicant and has been shown to be very useful in determining the effectiveness of the stimulation and to improve and program the device to suit the individual recipient.

Figure 2:
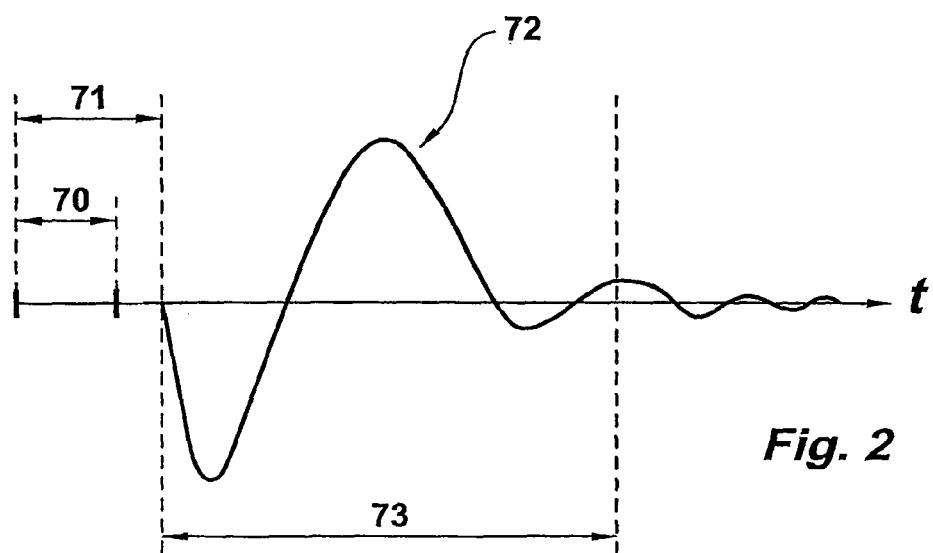
FIG. 2 illustrates a typical evoked neural response.

FIG. 2 illustrates a typical evoked neural response, which may arise in response to a stimulus applied by the electrode array 20 as depicted in FIG. 1. Period 70 in FIG. 2 illustrates a stimulation period, during which a stimulus is applied to an auditory nerve. The neural response 72 typically commences approximately 100 microseconds after the onset of the stimulus phase 70, as indicated by period 71. The duration of the more significant features of the response is around 1000 microseconds, as indicated by period 73, while the response measurement period or window is usually around 1.5 to 3 milliseconds.

Figure 3:
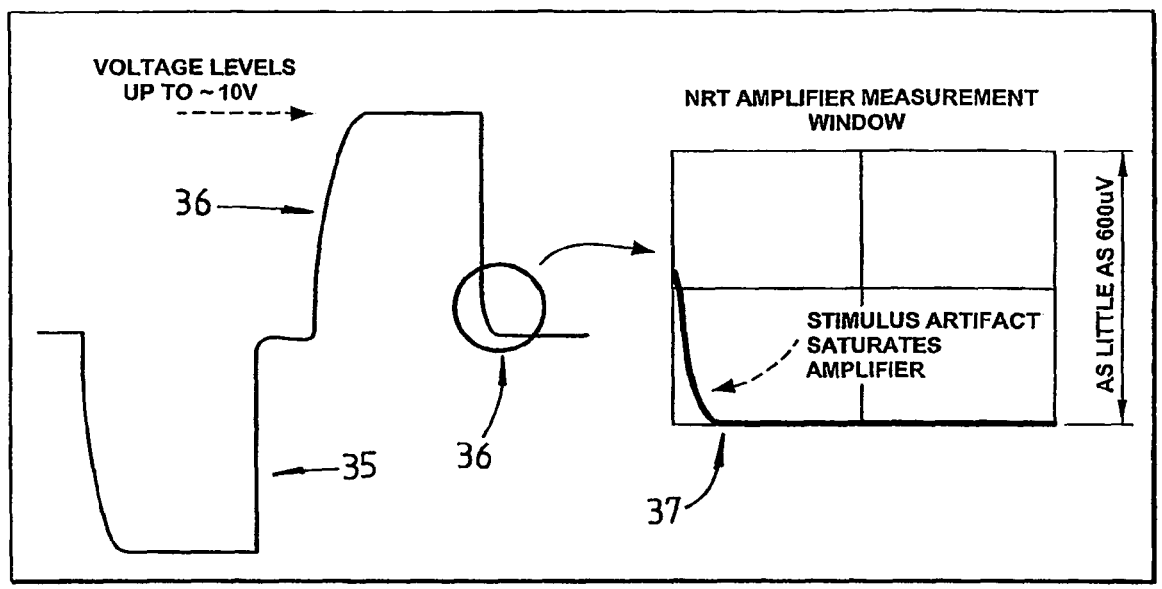
FIG. 3 illustrates stimulus voltages and saturation of an amplifier by a sensed signal, in a prior art system.

FIG. 3 illustrates the problem which may occur in such systems where stimulus artefacts exist and where a method such as the present invention is not used. A stimulus applied by the electrode array comprises a negative pulse 35 followed by a positive pulse 36, each pulse having an amplitude of up to 10V. During time 36, a significant stimulus artefact remains in the vicinity of the auditory nerve, causing relatively large stimulus artefact voltages to exist on the electrodes 25 of the electrode array 20. An amplifier operating at relatively high gain in attempting to resolve the small neural response, will therefore be saturated by the stimulus artefacts in the sensed signal, as shown at 37. Consequently, no useful information can be obtained from the amplifier due to the stimulus artefact.

Figure 4:
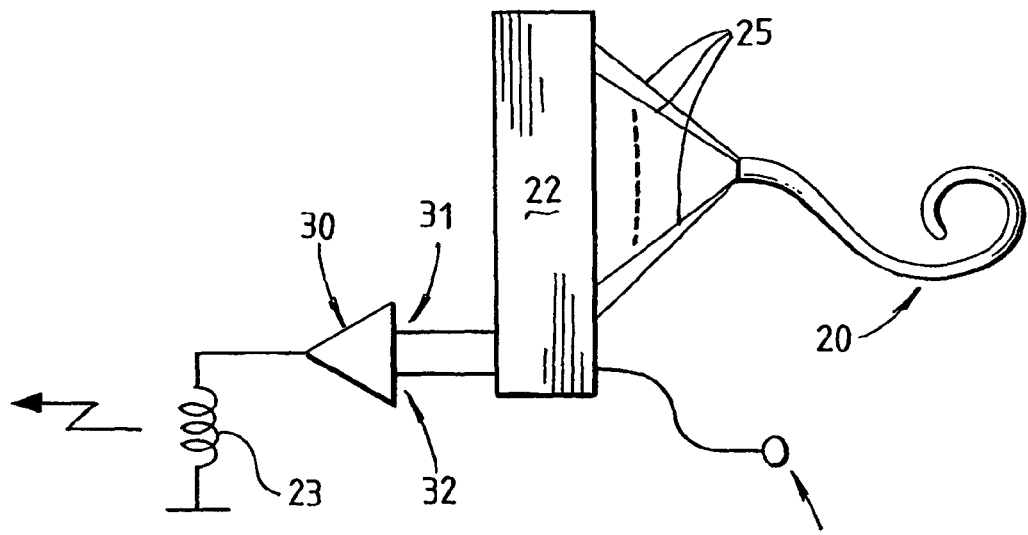
FIG. 4 is a pictorial circuit representation of portions of the implanted component of the cochlear implant of FIG. 1, in accordance with an embodiment of the present invention.

FIG. 4 is a pictorial circuit representation of portions of the implanted component of the cochlear implant of FIG. 1, in accordance with an embodiment of the present invention. When it is desired to measure a neural response evoked by application of a stimulus by the electrode array 20, a sensed signal is obtained by a sensor in the form of one or more of the intra-cochlear electrodes 25, which is often done with reference to a voltage on the extra-cochlear electrode 28. The sensed signal is passed to the signal input 31 of amplifier 30, and, in accordance with the present invention, the voltage applied to the reference input 32 of the amplifier is controlled throughout the measurement period. The output of the amplifier 31 is passed to coil 23 for transcutaneous transmission to an external coil for subsequent processing.

During measurement of the evoked neural response, the sensed signal from the electrode(s) 25, 28 is sampled at a high rate, which could be perhaps 20-50 kHz. In the present embodiment, the amplifier 30 is operated in a mode, whereby at the commencement of each sample period, the voltage at the reference input of the amplifier is set to be equal to the sensed signal. In the present embodiment, the reference voltage is maintained by a sample-and-hold circuit (not shown), the input of which is taken from the sensed signal.

By operating the amplifier 30 in such a mode, each sample measures only the change in the sensed signal which occurs during that sample period, and provides no information about the present dc-level of the sensed signal. Due to the high sampling rate, this change is relatively small, allowing the amplifier 30 to be operated with a high gain without saturating, and thus enabling higher resolution data to be extracted from the sensed signal. In the present embodiment, the sensed signal may be amplified by up to 75 dB.

Figure 5:
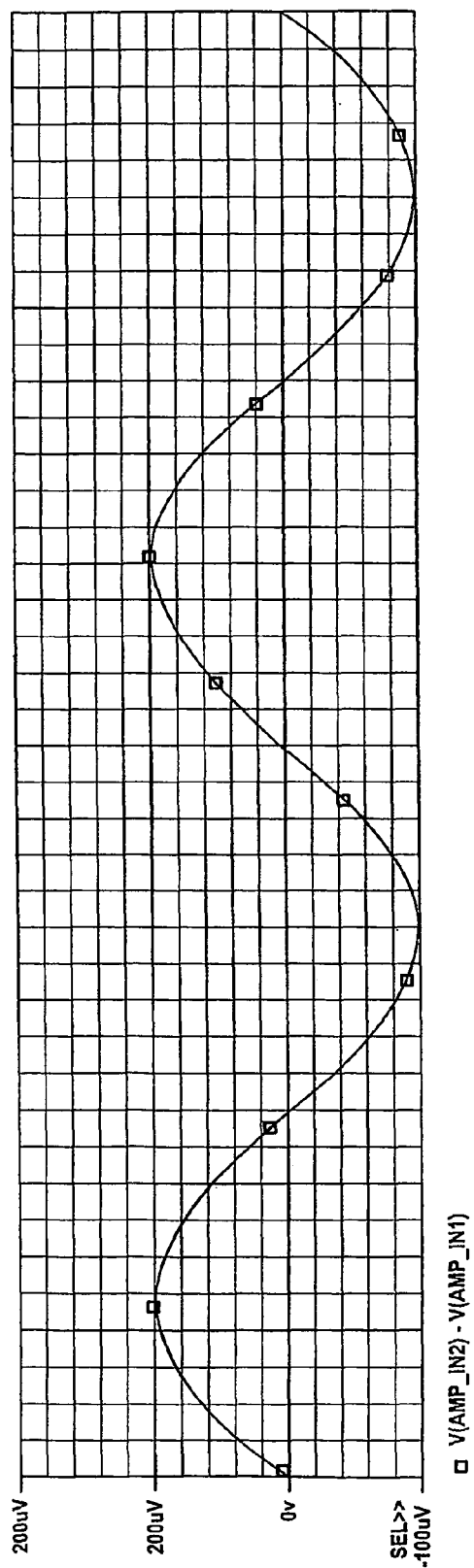
FIG. 5 illustrates the input and output waveforms of a high gain amplifier in both normal mode and the mode of the present invention.
Figure 5:
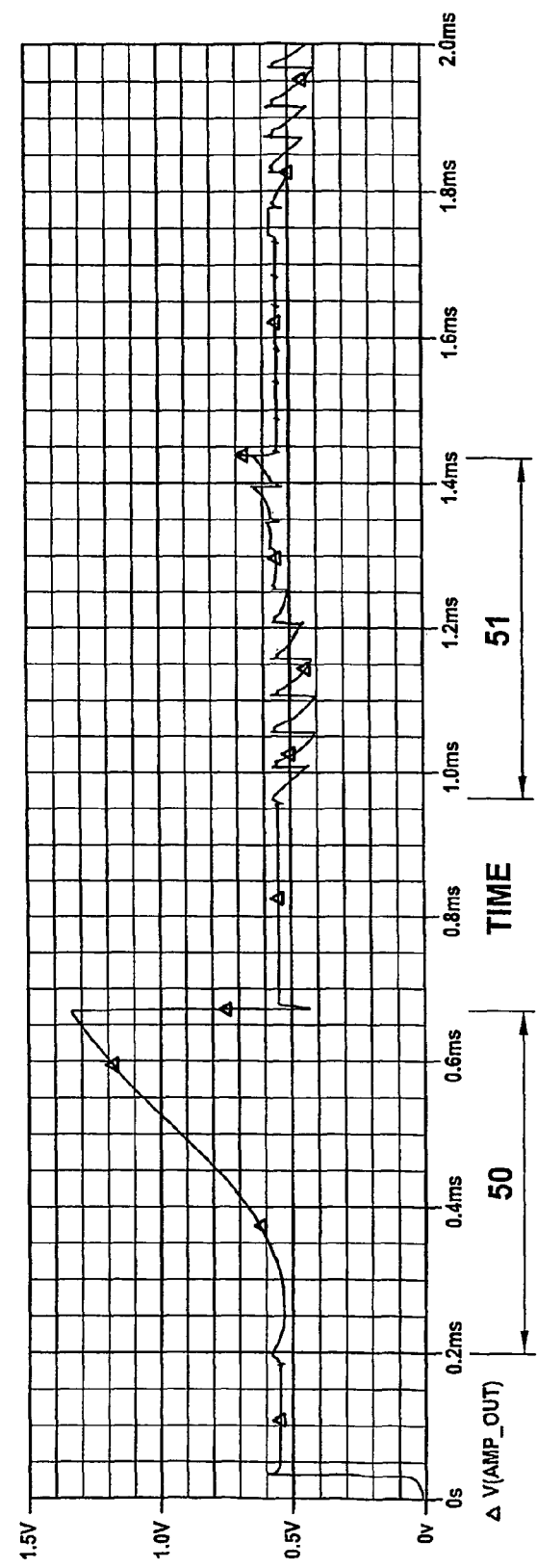

FIG. 5 illustrates the input and output waveforms of a high gain amplifier operating in both normal mode and the mode of the present invention. The input signal shown in the upper voltage chart is sinusoidal for illustrative purposes and has a peak-to-peak amplitude of 200 microvolts. Of course, a neural response would be expected to differ from this waveform, but would typically have an amplitude of a similar order. During period 50, the amplifier operates in normal mode and amplifies the input signal with reference to zero volts. During this period, the output signal shown in the lower chart has a peak to peak amplitude of around 0.9 volts. During period 51 the amplifier operates in the mode of the present invention, whereby the input signal is amplified with reference to a reference voltage which changes approximately every 50 microseconds, that is, at around 20 kHz. In this mode, the reference voltage is periodically changed to be equal to the present value of the input signal, such that over the ensuing 50 microseconds the amplifier only amplifies changes of the sensed signal from that value. Accordingly, the peak-to-peak amplitude of the output of the amplifier during period 51 is significantly smaller than during period 50. This allows a higher gain to be used when amplifying the input signal, while still avoiding saturation of the amplifier. Reconstruction of the output signal into a continuous waveform is a simple matter. Consequently, significantly more information may be extracted from the input signal by use of the mode of the present invention and higher amplification.

Figure 6:
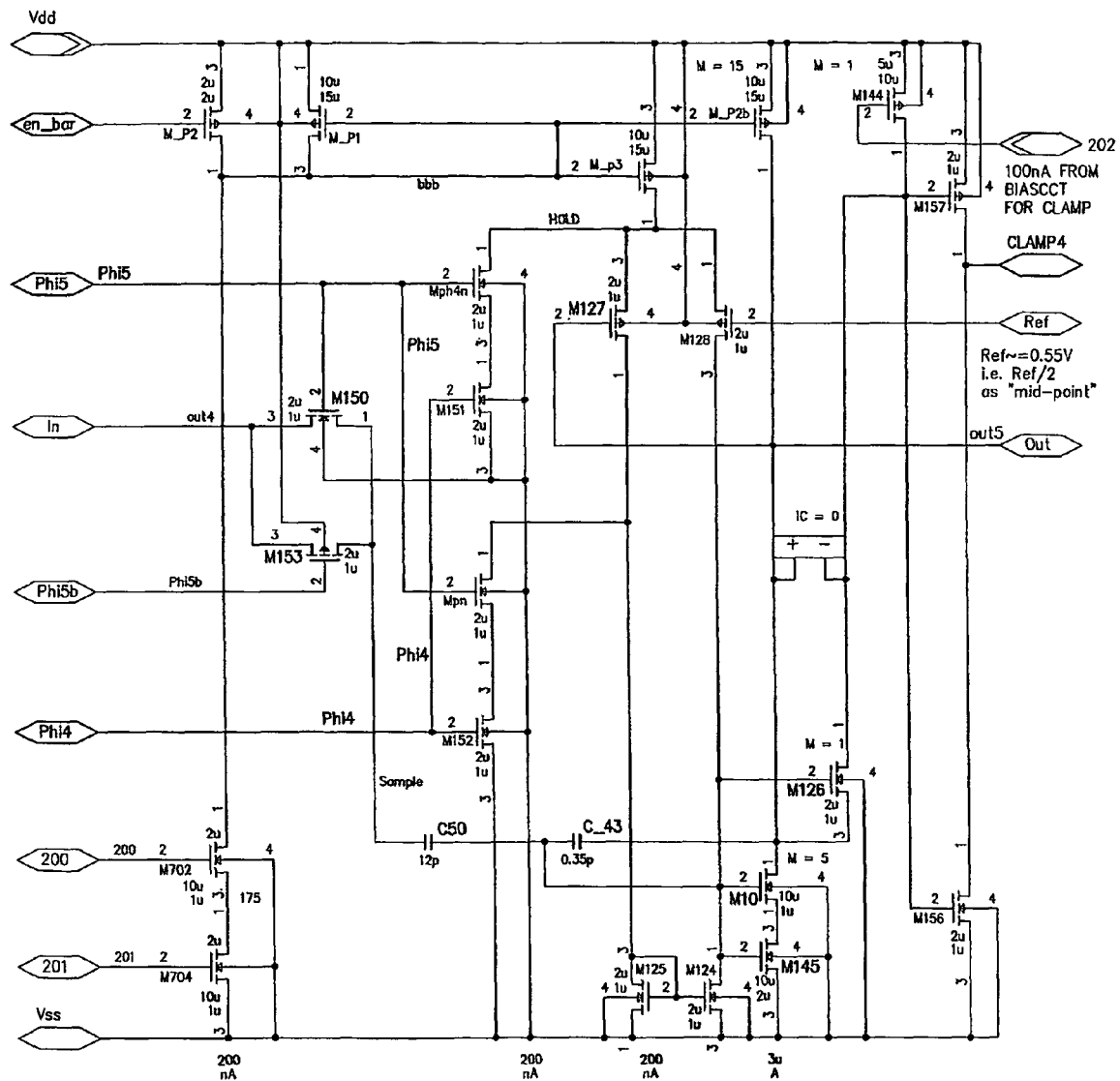
FIG. 6 is a circuit diagram of an amplifier stage for implementing the present invention.

FIG. 6 is a circuit diagram of a fourth stage of a multi-stage amplifier for implementing the mode of the present invention. The multi-stage amplifier is used for amplifying the differential electrode voltage (the neural signals) to a single ended output. It has very high selectable gain of 45, 55, 65 and 75 db. The multi-stage amplifier inputs are connected to the electrodes. Stage 1 is a differential in and differential out amplifier with a gain of 15 dB. Stage 2 is a differential in and single-ended output amplifier with a selectable gain of 15 dB or 1.5 dB. Stage 3 amplifies the signal from stage 2 by a selectable gain of 1 or 0.316.

Stage 4, shown in FIG. 6, amplifies the signal from stage 3 by a gain of 30. The mode of the present invention is implemented by this stage and can be applied selectively.

As stage 2 and stage 3 have alterable gain, the gain of the multi-stage amplifier may be selected to be 45 dB, 55 dB, 65 dB or 75 dB.

As it is intended to be implanted inside the body, the amplifier should have low power consumption to reduce the drain on the power requirements of the implant system. The sensed signal from the evoked neural response is typically of the order of 100 microvolts, and is typically superimposed on a much larger signal, the stimulus artefact. Thus the amplifier requires large input common mode rejection ratio, so that the stimulus artefacts, being the common mode input signals, can be largely cancelled out. Due to the large stimulus levels, the amplifier is typically held inactive until after the stimulus has concluded. However, due to the swift onset of the neural response, the amplifier must be able to be initialised very quickly after conclusion of the stimulus.

Further, as the stimulus artefact can have either a positive or negative slew depending on which electrodes are chosen to obtain the sensed signal, the amplifier must be capable of bipolar action.

The fourth stage amplifier, shown in FIG. 6, provides this capability. The amplifier is disabled when the en_bar is set low. This stage has an inverting amplifier with a gain of 30 obtained from the capacitor C50 and feedback capacitor C_43. The sample and hold function is performed by the transmission gate (M150 & M153). When phi5 is set high, the signal is passed through. While it is at low, the signal is held. Phi4 resets the quiescent voltage of the output to the reference voltage of the amplifier, when it is low. The reference voltage sets the quiescent output voltage. By altering the reference voltage of the amplifier, the mode of the present invention is enabled. When both Phi4 and Phi5 are high the voltage at the source of the transistor M127 is pulled to ground otherwise it is at its DC bias level. The differential pair and the gain transistor are never working at the same time. In this circuit either the differential pair are setting the dc bias level of the output to its dc level and the input signal is not defined or else the differential pair are not being used and one output of it is pulled to ground while the gain transistor M10 is operating. The differential pair sets the output to the reference level as follows. One side of the differential pair is connected to the reference, while the other side is connected to output. The active transistors M10, M145 act like the 2nd stage of OTA and there is unity gain feedback to close the loop. This ensures that output is set to ref when the differential pair is acting. Clamp4 goes high when the M126 starts to conduct. That is when the output voltage is one threshold lower than the input. The overload operates in one direction only. An overload (clamp4) is not truly necessary as the true amplifier output can itself be an indication of overload but clamp4 again is there for completeness.

The voltage waveforms of FIG. 5 shows the multi-stage amplifier input voltage and the corresponding output voltage. With such a circuit, a common mode rejection ratio of 40 dB can be achieved, and the mode of the present invention can be implemented.

While an embodiment has been described in which the reference voltage of the amplifier is altered at the commencement of every sample period, it is to be appreciated that in alternate embodiments of the present invention the reference voltage may be altered with more or less frequency and still provide the advantages of the present invention. Such embodiments are thus within the scope of the present invention.

Further, it is to be appreciated that the present invention may be used to advantage in conjunction with the neural response measurement method disclosed in International Application No. PCT/AU02/00500 by the present applicant. Such a stimulus artefact cancellation scheme may further enhance measurements which may be obtained by the system and method of the present invention.

Additionally, the present invention may also be used to particular advantage where the implanted portion of the prosthesis has processing capability, such as the system disclosed PCT/AU01/00769 by the present applicant. In such a system, processing of the sensed signal may be carried out entirely within the implant, thus avoiding the deleterious effects caused by noise of an RF link. Preferably, the RF link is inactivated throughout such processing in order to minimise or entirely eliminate cross-talk and other such noise-effects on the data quality produced by such processing. Given that such internal processing is typically carried out on-board at perhaps 1.2V, very little cross-talk or electromagnetic interference will exist, thus enabling significantly improved SNR to be obtained when processing the sensed signal. It is anticipated that such an improvement in the noise conditions may in fact enable measurements of brain stem responses reflected down the auditory nerve to be measured, in addition to measurement of the evoked neural response itself.

Such internal processing may comprise repeatedly applying a stimulus and measuring the evoked neural response, and averaging the measured responses. For example, 100 repetitions of applying the stimulus and measuring the response may be carried out in order to produce an averaged response. Once the averaged response is obtained, a transcutaneous RF link may then be activated and the averaged response transmitted externally for analysis or subsequent processing. The internal processing may alternatively be carried out as disclosed in International Application No. PCT/AU02/00500 by the present applicant in respect of an external processing procedure.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An evoked neural response measuring device comprising:
    a first implantable subsystem comprising an amplifier having a reference voltage input and a signal input, and an electrode array configured to provide stimulation to the auditory nerve and further configured to generate a response signal corresponding to an evoked neural response of the auditory nerve to the stimulation;
    wherein said first implantable subsystem is configured to sample the response signal at a first time to obtain a first sampled value of the response signal, and to provide the first sampled value of the response signal to the reference voltage input, and wherein the amplifier is configured to amplify differences between the response signal and the first sampled value of the response signal at a plurality of times to thereby obtain a changing first output signal representing at least a first portion of an amplified version of the evoked neural response of the auditory nerve.

2. The device of claim 1, wherein the first implantable subsystem further comprises:
    an extra-cochlear electrode configured for detection of the response signal, wherein the extra-cochlear electrode works in concert with the electrode array for detection of the response signal.

3. The device of claim 1, wherein the first implantable subsystem is further configured to provide the first sampled value of the response signal to the reference voltage input at the beginning of a first sample period, to sample said response signal at a second time to obtain a second sampled value of the response signal, and to provide the second sampled value of the response signal to the reference voltage input at the beginning of a second sample period.

4. The device of claim 3, wherein the first subsystem further comprises:
    a sample-and-hold circuit configured to receive the response signal, to provide the first sampled value of the response signal to the reference voltage input at the beginning of the first sample period, and to provide the second sampled valued of the response signal to the reference voltage input at the beginning of the second sample period.

5. The device of claim 1, further comprising:
a second subsystem configured to reconstruct at least the first output signal into a continuous waveform.

6. A method of measuring an evoked neural response using a cochlear implant comprising:
stimulating a portion of an auditory nerve to elicit an evoked neural response via an electrode array of an implanted subsystem comprising an amplifier having a reference voltage input and a signal input;
sensing a response signal corresponding to the evoked neural response using at least the electrode array;
sampling the response signal at a first time to obtain a first sampled value of the response signal;
providing the first sampled value of the response signal to the reference voltage input;
providing the response signal to the signal input; and
amplifying differences between the response signal and the first sampled value of the response signal at a plurality of times to thereby obtain a changing first output signal representing at least a first portion of an amplified version of the evoked neural response.

7. The method of claim 6, wherein sensing the response signal corresponding to the evoked neural response using at least the electrode array comprises:
sensing the response signal corresponding to the evoked neural response using an extra-cochlear electrode and at least one electrode of the electrode array.

8. The method of claim 6, wherein the first sampled value of the response signal is provided to the reference voltage input at the beginning of a first sample period, the method further comprising:
sampling the response signal at a second time to obtain a second sampled value of the response signal; and
providing the second sampled value of the response signal to the reference voltage input at the beginning of a second sample period.

9. The method of claim 8, wherein the first output signal is obtained during a first sample period,
the method further comprising:
during the second sample period, amplifying differences between the response signal and the second sampled value of the response signal at a plurality of times to thereby obtain a changing second output signal representing at least a second portion of the amplified version of the evoked neural response, and
reconstructing at least the first and second output signals into a continuous waveform.

10. The method of claim 6, further comprising:
reconstructing at least the first output signal into a continuous waveform.

11. The method of claim 6, wherein sensing the response signal corresponding to the evoked neural response using at least the electrode array comprises:
utilizing one or more electrodes of the electrode array to sense the response signal.

12. A device for measuring an evoked neural response in a cochlear implant comprising:
means for stimulating a portion of an auditory nerve via an electrode array to elicit an evoked neural response via an implanted subsystem comprising an amplifier having a reference voltage input and a signal input;
means for sensing a response signal corresponding to the evoked neural response using at least the electrode array;
means for sampling the response signal to obtain a first sampled value of the response signal;
means for providing the first sampled value of the response signal to the reference voltage input;
means for providing the response signal to the signal input; and
means for amplifying differences between the response signal and the first sampled value of the response signal at a plurality of times to thereby obtain a changing first output signal representing at least a first portion of an amplified version of the evoked neural response.

13. The device of claim 12, wherein the means for sensing the response signal corresponding to the evoked neural response using at least the electrode array comprises:
means for sensing the response signal corresponding to the evoked neural response using an extra-cochlear electrode and at least one electrode of the electrode array.

14. The device of claim 12, wherein the means for sampling the response signal samples the response signal at a first time to obtain the first sampled value of the response signal, and comprises:
means for sampling the response signal at a second time to obtain a second sampled value of the response signal.

15. The device of claim 14, wherein the means for providing the first sampled value of the response signal to the reference voltage input comprises:
means for providing the first sampled value of the response signal to the reference voltage input at the beginning of a first sample period; and
means for providing the second sampled value of the response signal to the reference voltage input at the beginning of a second sample period.

16. The device of claim 15, wherein the amplifying means comprises:
means for amplifying differences between the response signal and the first sampled value of the response signal at a plurality of times during the first sample period to thereby obtain the changing first output signal; and
means for amplifying differences between the response signal and the second sampled value of the response signal at a plurality of times during the second sample period to thereby obtain a second changing output signal representing at least a second portion of the amplified version of the evoked neural response.

17. The device of claim 12, further comprising:
means for reconstructing at least the first output signal into a continuous waveform.

18. The device of claim 5, wherein the changing first output signal is obtained during the first sample period; wherein said amplifier is further configured to amplify differences between the response signal and the second sampled value of the response signal at a plurality of times during the second sample period to thereby obtain a changing second output signal representing at least a second portion of the amplified version of the evoked neural response of the auditory nerve; and wherein said second subsystem is configured to reconstruct at least the first and second output signals into a continuous waveform.

* * * * *